United States Patent
Woloschek et al.

(10) Patent No.: US 11,842,812 B2
(45) Date of Patent: Dec. 12, 2023

(54) LOCATION-BASED USER AUTHORIZATION FOR AN INFANT CARE DEVICE

(71) Applicant: GE Precision Healthcare LLC, Wauwatosa, WI (US)

(72) Inventors: Steven J. Woloschek, Wauwatosa, WI (US); Steven M. Falk, Wauwatosa, WI (US); Karen P. Starr, Wauwatosa, WI (US); Elizabeth K. Devins, Wauwatosa, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 1182 days.

(21) Appl. No.: 16/455,007

(22) Filed: Jun. 27, 2019

(65) Prior Publication Data

US 2020/0411177 A1    Dec. 31, 2020

(51) Int. Cl.
*G16H 40/63* (2018.01)
*A61F 7/00* (2006.01)
(Continued)

(52) U.S. Cl.
CPC ........... *G16H 40/63* (2018.01); *A61B 5/6888* (2013.01); *A61F 7/0053* (2013.01); *A61G 11/00* (2013.01);
(Continued)

(58) Field of Classification Search
CPC .............. G16H 40/63; A61B 5/6888; A61B 2503/045; A61B 90/98; A61F 7/0053;
(Continued)

(56) References Cited

U.S. PATENT DOCUMENTS

| 4,038,973 A | 8/1977 | Moore |
| 4,137,979 A | 2/1979 | Itani |

(Continued)

FOREIGN PATENT DOCUMENTS

| KR | 10-1587924 B1 | 1/2016 |
| WO | 2005079122 A1 | 8/2005 |
| WO | 2014209697 A1 | 12/2014 |

OTHER PUBLICATIONS

Kamel Boulos MN, Berry G. Real-time locating systems (RTLS) in healthcare: a condensed primer. Int J Health Geogr. Jun. 28, 2012;11:25. doi: 10.1186/1476-072X-11-25. PMID: 22741760; PMCID: PMC3408320 (Year: 2012).*

(Continued)

*Primary Examiner* — Sunita Reddy
(74) *Attorney, Agent, or Firm* — ANDRUS INTELLECTUAL PROPERTY LAW, LLP

(57) ABSTRACT

A method of controlling an infant care device includes identifying, via a location tracking system, a device location of the infant care device within a care facility by locating a device location tag on the infant care device, and also identifying any local clinician tags worn by a clinician within a predetermined area around the device location. The local clinician tags are compared to a list of authorized clinician tags to identify whether at least one local authorized clinician tag is within the predetermined area around the infant care device. User input is received at a user interface associated with the infant care device to modify operation of the infant care device. Operation of the infant care device is modified based on the user input only if at least one local authorized clinician tag is within the predetermined area around the infant care device at the time of receiving the user input.

9 Claims, 5 Drawing Sheets

(51) Int. Cl.
*A61G 11/00* (2006.01)
*A61B 5/00* (2006.01)

(52) U.S. Cl.
CPC . *A61B 2503/045* (2013.01); *A61F 2007/0062* (2013.01); *A61F 2007/0093* (2013.01); *A61G 2203/20* (2013.01)

(58) Field of Classification Search
CPC ..... A61F 2007/0062; A61F 2007/0093; A61G 11/00; A61G 2203/20; G07C 9/20; G07C 9/28
USPC .................................................. 600/21–22
See application file for complete search history.

(56) References Cited

U.S. PATENT DOCUMENTS

| | | | |
|---|---|---|---|
| 4,159,521 A | 6/1979 | Hall et al. | |
| 4,181,946 A | 1/1980 | Loshbough et al. | |
| 4,301,879 A | 11/1981 | Dubow | |
| 4,313,510 A | 2/1982 | Tomlinson, Jr. | |
| 4,330,837 A | 5/1982 | Itani | |
| 4,423,792 A | 1/1984 | Cowan | |
| 5,376,761 A | 12/1994 | Koch et al. | |
| 5,832,417 A | 11/1998 | Petrucelli et al. | |
| 6,215,078 B1 | 4/2001 | Torres et al. | |
| 6,354,996 B1 | 3/2002 | Drinan et al. | |
| 6,434,258 B2 | 8/2002 | Wiens | |
| 6,617,530 B1 | 9/2003 | Lin | |
| 6,679,854 B2 | 1/2004 | Honda et al. | |
| 7,265,301 B2 | 9/2007 | Simberg | |
| 7,357,811 B2 | 4/2008 | Dykes et al. | |
| 7,364,539 B2 | 4/2008 | Mackin et al. | |
| 7,927,269 B2 | 4/2011 | Ten Eyck et al. | |
| 7,982,140 B2 | 7/2011 | Taylor et al. | |
| 7,994,439 B2 | 8/2011 | Daniels et al. | |
| 8,018,584 B1 | 9/2011 | Amir | |
| 8,139,945 B1 | 3/2012 | Amir et al. | |
| 8,168,898 B2 | 5/2012 | Reber et al. | |
| 8,310,364 B2 | 11/2012 | Derks et al. | |
| 8,475,367 B1 | 7/2013 | Yuen et al. | |
| 8,514,071 B2 | 8/2013 | Derks et al. | |
| 8,536,470 B2 | 9/2013 | Sato et al. | |
| 8,585,574 B2 | 11/2013 | Ten Eyck et al. | |
| 8,599,025 B2 | 12/2013 | Cipriano | |
| 8,617,043 B2 | 12/2013 | Ten Eyck et al. | |
| 8,620,682 B2 | 12/2013 | Bechtel et al. | |
| 8,633,806 B2 | 1/2014 | Amir | |
| 8,708,883 B2 | 4/2014 | Ten Eyck et al. | |
| 8,795,151 B2 | 8/2014 | Falk et al. | |
| 8,978,181 B2 | 3/2015 | Menke et al. | |
| 9,055,928 B2 | 6/2015 | McCombie et al. | |
| 9,219,984 B1 | 12/2015 | Amir | |
| 9,306,665 B1 | 4/2016 | Amir | |
| 9,341,700 B2 | 5/2016 | Amir et al. | |
| 10,535,244 B2 | 1/2020 | Treacy et al. | |
| 2002/0196141 A1* | 12/2002 | Boone | A61B 5/742 340/540 |
| 2005/0215845 A1* | 9/2005 | Mahony | A61B 5/002 600/22 |
| 2006/0181424 A1* | 8/2006 | Graves | G16H 40/20 600/300 |
| 2007/0074911 A1 | 4/2007 | Simberg | |
| 2007/0136102 A1 | 6/2007 | Rodgers | |
| 2007/0162304 A1 | 7/2007 | Rodgers | |
| 2009/0044987 A1 | 2/2009 | Taylor et al. | |
| 2011/0105854 A1 | 5/2011 | Kiani et al. | |
| 2012/0157757 A1 | 6/2012 | Ten Eyck et al. | |
| 2012/0169501 A1 | 7/2012 | Cipriano | |
| 2013/0158339 A1 | 6/2013 | Cipriano et al. | |
| 2014/0077956 A1 | 3/2014 | Sampath et al. | |
| 2014/0145848 A1 | 5/2014 | Amir | |
| 2014/0247137 A1 | 9/2014 | Proud et al. | |
| 2015/0254964 A1* | 9/2015 | Raichman | A61G 11/00 340/573.1 |
| 2015/0269824 A1 | 9/2015 | Zhang | |
| 2016/0069735 A1 | 3/2016 | Underwood | |
| 2016/0140827 A1 | 5/2016 | Derenne et al. | |
| 2016/0157735 A1 | 6/2016 | Zhang | |
| 2018/0168903 A1* | 6/2018 | Underwood | H04L 67/12 |
| 2019/0320899 A1* | 10/2019 | Mukherjee | G16H 10/60 |
| 2020/0318842 A1* | 10/2020 | Hall, Jr. | F24F 11/88 |

OTHER PUBLICATIONS

Encompass, Simple, fast, flexible, cost-efficient: A new paradigm in real-time location systems Bluetooth® low energy wireless technology leveraging hospitals' existing Wi-Fi® opens doors to wider adoption of RTLS and better management of mobile assets. Gillan,Cannell,Woodburn,Elhassan. Zebra Tech&GE (Year: 2017).*

* cited by examiner

LOCATION-BASED USER AUTHORIZATION FOR AN INFANT CARE DEVICE

BACKGROUND

The present disclosure generally relates to medical devices and, more specifically, to infant care devices and control methods implementing user authentication for infant care devices.

In patient care environments, often times multiple patient care devices are operating on each patient, and multiple patients may be under medical care within a particular care environment. In certain care environments, multiple patients are positioned nearby one another, such as in a recovery room or in a neonatal care unit, to provide a few examples. Patient physiological data and actions performed by clinicians interacting with the medical care devices are tracked in the patient medical record and/or in audit logs associated with each care device. Various care devices are used in medical care environments. In infant care environment, for example, various infant care devices may include incubators, warmers, physiological monitoring devices attached to the infant, etc. In neonatal units and other infant care units, the concentration of care devices is especially high because the patients are small and multiple infants may be in individual rooms or co located in open bays or pods where they are cared for by multiple care providers.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of a method of controlling an infant care device includes identifying, via a location tracking system, a device location of the infant care device within a care facility by locating a device location tag on the infant care device, and also identifying any local clinician tags worn by a clinician within a predetermined area around the device location. The local clinician tags are compared to a list of authorized clinician tags to identify whether at least one local authorized clinician tag is within the predetermined area around the infant care device. User input is received at a user interface associated with the infant care device to modify operation of the infant care device. Operation of the infant care device is modified based on the user input only if at least one local authorized clinician tag is within the predetermined area around the infant care device at the time of receiving the user input.

An infant incubator or warmer includes a platform configured to support an infant, an environmental control system configured to control a temperature and/or humidity of an environment around the infant, a user interface configured to receive user input to control operation of the infant incubator or warmer, and a controller configured to receive the user inputs from the user interface and to control operation of the infant incubator or warmer. The controller is configured to receive a user input from the user interface to control operation of the infant incubator or warmer and determine whether at least one authorized clinician is within a predetermined area around the infant incubator or warmer based on clinician location information from a location tracking system. If at least one authorized clinician is within the predetermined area around the infant incubator or warmer, the controller modifies operation of the infant incubator or warmer based on the user input. If, on the other hand, no authorized clinician is within the predetermined area around the infant incubator or warmer, the controller does not modify operation of the infant incubator or warmer based on the user input.

An infant care system includes an infant care device having a controller that controls operation of the infant care device and a user interface configured to receive user input to control operation of the infant care device. The system further includes a device location tag on the infant care device and multiple clinician location tags, each clinician location tag configured to be worn on a clinician. A location tracking system included in the system is configured to identify a device location of the infant care device within a care facility by locating the device location tag, and identify any local clinician tags, wherein a local clinician tag is one of the multiple clinician location tags that is within a predetermined area around the device location. A location authorization module comprises software executable to compare the local clinician tags to a list of authorized clinicians to identify at least one local authorized clinician tag. The controller of the infant care device is configured to modify operation of the infant care device based on the user input only when the at least one local authorized clinician tag is identified within the predetermined area around the infant care device.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
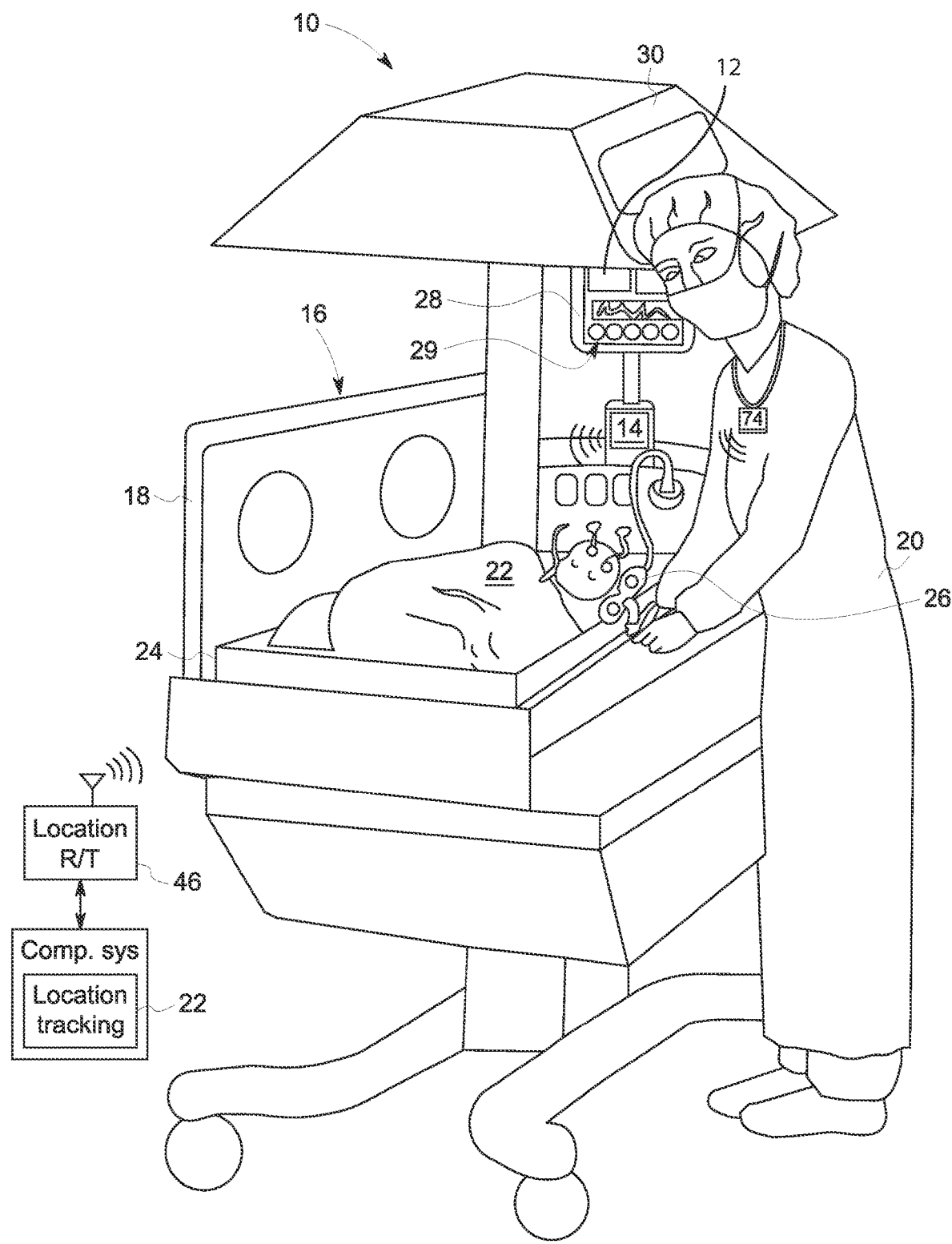
FIG. 1 depicts an exemplary embodiment of an infant care device and system with location based user authentication according to one embodiment of the present disclosure.

The inventors have recognized that potential security and patient safety issues exist with current medical care devices, and for infant care devices in particular. Medical devices often do not integrate user authorization or authentication functionality, and thus do not require user authentication or authorization to provide access to device control functionality, patient identification information, and/or to modify patient medical records. One barrier to implementing user authentication is that it can present delays to providing medical care, which is particularly problematic in urgent care situations. However, a drawback to not requiring user authentication or authorization is that unauthorized persons may gain access to sensitive patient information, such as patient identification information and/or medical record access. Similarly, unauthorized persons may gain access to control the care devices. For example, unauthorized personnel may have access to modify the functionality of devices and/or modify a patient's medical record, such as annotations provided through the care device. Infant care devices, in particular, may be placed in various types of care locations (e.g., a mother's room or a NICU), some of which allow unrestricted access for visitors and non-medical personal. Where user authentication is not implemented on a care device in these environments, these individuals have access to operate or make changes to the device.

While any existing devices do store such control modifications in an audit log, where no user authorization or authentication is required, no record is kept regarding who made the change. Thus, the lack of authentication is problematic from a patient safety standpoint, as well as from a record keeping standpoint.

In view of the foregoing challenges and problems in the relevant art recognized by the inventors, the inventors have recognized that improved methods of controlling care devices, particularly infant care devices, are desired to implement user authentication prior to authorizing control over the care devices and/or access to patient data that can be displayed on the user interface of the care device. Furthermore, the inventors have recognized that such authentication should require minimal, if any, clinician interaction with the device in order to gain authorization. For example, requiring a clinician to enter a password or otherwise manually input authentication information would overly inhibit patient care. The inventors have recognized that methods of user authentication based on voice recognition and wake words are problematic in environments where multiple care devices are in close proximity to one another. For example, in infant care areas where multiple incubators or infant warmers are operating to care for infants, a challenge is posed because multiple infant care devices would detect the wake word. This would lead to unintended devices being "woken up" and made available for user control, where only a single device is being targeted and should be granted authorization. This could lead to unintended to improper changes to devices other than the device of interest to the clinician.

In view of the above, the inventors developed the disclosed method and system that utilizes location tracking systems, such as real time location tracking systems (RTLS), for purposes of care device authentication. In one embodiment, an infant care device includes a controller configured to determine whether at least one authorized clinician is within a predetermined distance of the infant incubator before permitting, or acting on, any control command to change operation of the device. For example, the infant care device may be an infant incubator or warmer having a micro environment maintained by an environmental control system. The clinician proximity determination is based on clinician location information determined at and/or received from a location tracking system.

If at least one authorized clinician is within the predetermined distance of the infant care device, then the controller permits modification of the infant care device operation based on user input provided at a user interface. If no authorized clinician is within the predetermined distance of the infant care device, then no user control is permitted to modify operation of the infant care device. Various other methods and implementations may be utilized to determine whether an authorized clinician is present at the location of the infant care device in order to accurately and effectively authorize control over the infant care device and prevent unauthorized persons from providing such control outside of the close supervision of an authorized person. Additionally, the disclosed system and method may provide automatic tracking of control inputs and changes to the care device without requiring any additional work or input on behalf of the authorized clinician. Namely, modifications to the device functionality, including changes in device settings and inputting annotations to a medical record, to provide a few examples, are logged with the at least one local authorized clinicians identified at the time that the user input was received instructing those modifications.

FIG. 1 illustrates one embodiment of an infant care device 10 that incorporates the location-based user authentication according to the present disclosure. In the embodiment, the infant care device 10 may be located within a neonatal care unit where other infant care devices 10 are co-located housing different infants. The infant care system 10 is moveable and thus may alternatively be located within a mother's room where family members and/or visitors may also be located. Thus, as described above, there is a particular need for infant care devices to implement user identification and authorization before enabling control over the functionality of the care device or display for a modification of any medical information for the infant. The authorization utilizes a location tracking system 40 that tracks the location of the infant care device 10 and one or more clinicians 20 within the care environment (see also FIG. 2). Location authorization software is utilized on or in conjunction with the location tracking system in order to determine whether any clinicians detected within a predetermined distance of the infant care device are on a list of authorized clinicians permitted to provide care to the infant housed therein or otherwise associated therewith.

The infant care apparatus 10 shown in FIG. 1 could be many different types of devices, such as an incubator-type infant care apparatus or a patient warmer. The incubator-type device 10 shown in FIG. 1 defines a microenvironment 16 in which the patient rests and receives therapy, including heating, humidity, and possible oxygen enrichment.

The sides 18 of the infant care device 10 can be lowered such that a clinician 20 can have access to an infant 22 positioned on a platform 24. Various different patient sensors 26 can be attached to the infant such that the infant care device 10 can monitor physiological parameters from the infant. Thus, the infant care device 10 may include one or more physiological monitors monitoring the infant 22. The monitored physiological parameters are shown on a display 28 and can be viewed by the clinician 20. As illustrated in FIG. 1, a number of devices may be positioned on the platform 24 along with the infant 22, such as intravenous tubes, pillows, blankets, patient sensors, and other similar components. In certain embodiments, a controller 12 of the care device 10 may control functionality of one or more of these devices or components. In the embodiment shown in FIG. 1, a radiant heating hood 30 is positioned above the infant 22 and heats the infant as desired. As described previously, it is desirable that the infant 22 remain within the microenvironment created by infant care device 10 such that the patient remains warm and is disturbed as infrequently as possible.

Figure 2:
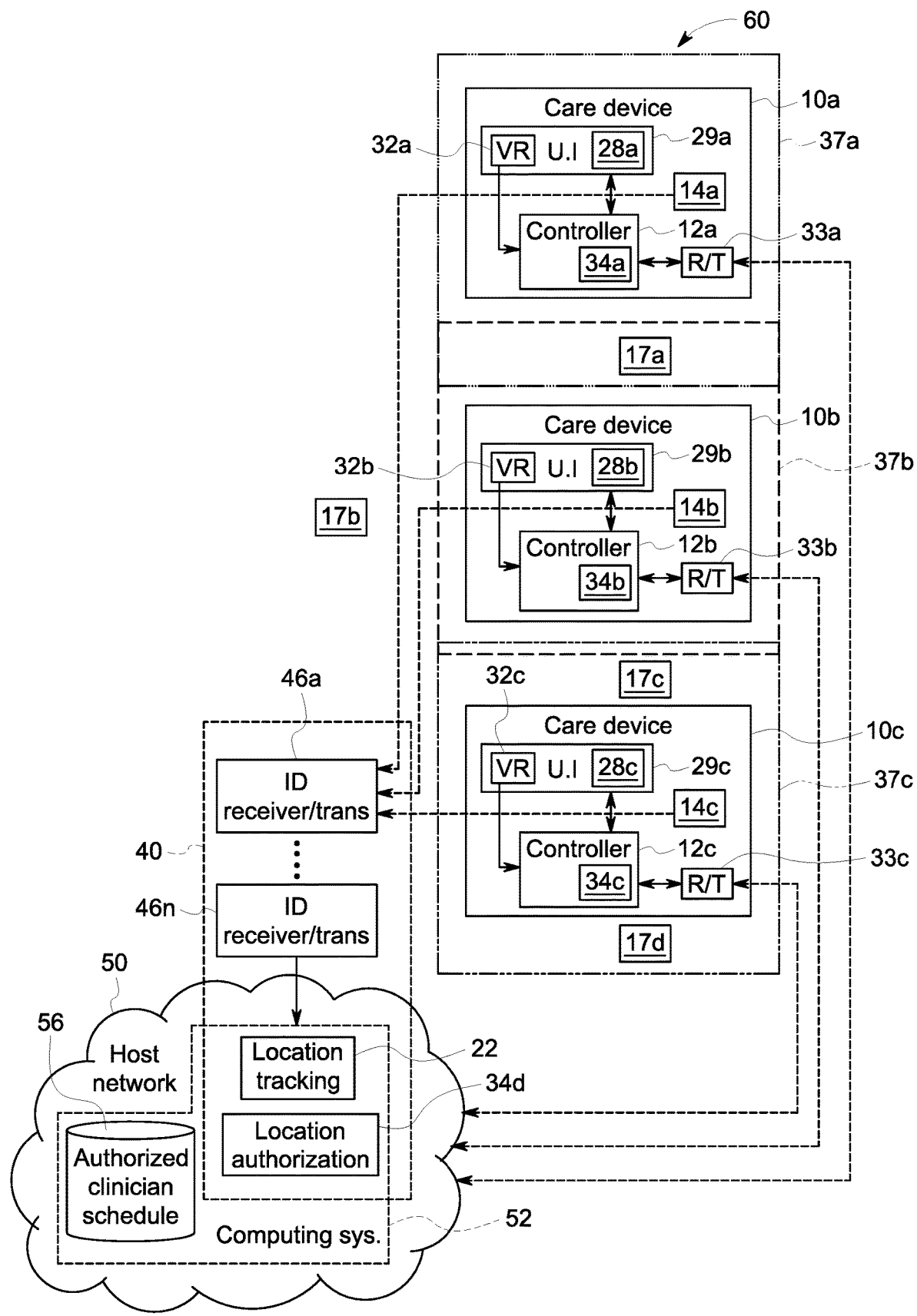
FIG. 2 is a schematic diagram of an embodiment of an infant care system according to the present disclosure.

With reference also to FIG. 2, the location tracking system may be, for example, a real time location system (RTLS) that provides immediate and continuous tracking of tagged assets or items. To provide just one example, the location tracking system 40 may include an Encompass™ hospital asset management solution by GE Healthcare. In various examples, the location tracking system 40 includes one or more receiver/transmitters 46a-46n, or beacons, that wirelessly communicate with tags, including device location tags 14 on infant care devices 10 and clinician location tags 17 worn by clinicians. In one embodiment, the location tags 14, 17 emit an identification signal that is detected by the receiver transmitters 46 within the location tracking system 40. For instance, the device location tags 14a-14c associated with each of the care devices 10a-10c may each transmit an identification signal that is associated with the respective care device 10a-10c within the location tracking system 40. Similarly, each clinician location tag 17a-17d may transmit a clinician identification signal that is associated with a respective clinician by the location tracking system 40. The location tracking system 40 receives the transmitted identification signals and determines a respective location of the person or device associated with that tag. Namely, since each clinician location tag 17a-17d is worn by an associated clinician, the location of the tag 17a-17d indicates the location of that clinician. Similarly, the device locations 14a-14c are fixed to the infant care devices 10a-10c, and thus the identified location of the tags 14a-14c can be used to track the location of the respective care devices 10a-10c associated with the transmission generated by that tag.

A plurality of identification receivers 46a-46n are placed at known locations throughout a care facility. The identification (ID) signal transmitted by each location tag 14, 17 is thus received by one of the identification receivers 46a-46n closest to, or otherwise arranged to receive transmissions from, identification transmitters at that particular location. Each identification receiver 46a-46n then communicates the identification signal, along with its own receiver identification, to a location tracking module 22 that monitors and determines the patient location for the location tracking system 40 within the care facility. For example, the identification receiver 46a, 46n may communicate the received ID signal from the tag and its own ID to a host network 30 for the care facility.

The location tracking module 22, which is a software module executable on one or more computing devices in the system 60, then determines a device location or a clinician location based on which identification receiver 46a-46n receives the identification signal for from one or more of the device tags 14a-14c or clinician tags 17a-17d. Specifically, the location tracking module 22 accesses a map or database of the care facility where each identification receiver 46a-46n is associated with a particular location in the care facility. The database associating each identification receiver 46a-46n with a location in the care facility may be, for example, uploaded and stored in the computing system 52 of the host network 50 as part of the system configuration.

For example, one or more identification receivers 46 may be provided in each care environment, such as each room, and multiple identification receivers 46 may be located in hallways. The system is configured such that the identification signal emitted by the one or more tags 14, 17 on the device/clinician is picked up by one of the identification receivers 46, thereby establishing the current location of that device or clinician associated with the transmitted ID.

The care system 60 includes location authorization software configured to utilize the location information and identify whether authorized clinicians are engaged in caring for an infant at a respective care device 10a-10c. Specifically, one or more location authorization modules 34 are executable, such as on a controller of a care device, to determine whether the clinician locations identified by the location tracking system 40 are within a predetermined area 37 around a care device.

With reference to FIG. 2, a predetermined area 37a-37c is defined with respect to each care device 10a-10c. The predetermined area 37a-37c may be defined based on the type of care device and/or based on the environment, or location, of the care device 10a-10c. For example, the predetermined area 37 may be defined as a predetermined distance around a care device, such as an appropriate distance range that a clinician would be located within if providing care to the infant 22 associated therewith. For an incubator or warmer care device 10, the predefined distance may be in the range of 2-3 feet, for example, but may be larger or smaller depending on the application, the size of the incubator or warmer, the density of other devices in the area, etc. In various embodiments, the predetermined area 37 may be symmetric around the care device 10 or asymmetric. For example, the predetermined area 37 may be defined only on each lateral side of the incubator or warmer, which is where clinicians typically stand when caring for an infant 22 in the incubator or warmer. A person having ordinary skill in the art will understand in light of this disclosure that the predetermined area 37 may be defined differently for various types of care devices and as may be appropriate for certain care environments.

The location authorization module 34 is configured to identify which, if any, clinician tags 17a-17d are within the predetermined area 37a-37c of any care device 10a-10c. The location authorization module 34 identifies any clinician tags 17a-17d that are within the predetermined area around a device location defined with respect to a device location tag 14a-14c (referred to herein as a "local clinician tag").

The location clinicians tags are then compared to a list of authorized clinician tags, which is to say the clinician IDs transmitted thereby, to identify whether any of the local clinician tags are associated with an authorized individual permitted to manipulate the care device 10a-10c. Local clinician tags that match a clinician identification on the list of authorized clinician tags are referred to herein as "local authorized clinician tags." While a local authorized clinician tag is detected for a respective care device 10a-10c, a clinician can modify operation of that care device, such as via the user interface 29a-29c. For example, a clinician may modify control settings for the care device 10a-10c, such as to modify the environmental control parameters for the microenvironment 16 or to modify monitoring parameters for a patient monitor and/or sensors 26 attached to the infant 22. To provide additional examples, the clinician may modify the information provided on the display 28 of the incubator or other care device, such as to view patient identification information or other patient medical record information.

In certain examples, the clinician may utilize the user interface 29 to add or modify information stored in the infant's medical record, such as to annotate and/or store physiological data collected by the patient monitors and/or other devices or systems associated with the incubator or patient warmer. The user interface 29 includes a display 28, which may be a touch screen, and may further include any number of other user input devices or elements through which a clinician can provide user input, such as a keypad, a keyboard, switches, push buttons, or the like. The user interface 29 may further include a voice recognition system 32. For example, the voice recognition system 32 may be programmed to receive and recognized auditory commands or inputs from the list of authorized clinicians. Such voice recognition systems and software are available, such as for example Dragon® software by Nuance®. In certain embodiments, the user interface 29 may be further configured to perform voice authentication, and thus may be configured to recognize voice signatures, or voice biometrics, of the authorized clinicians to thereby provide voice authentication interfaces. Accordingly, each care device 10a-10c may incorporate a voice recognition system 32a-32c that receives auditory commands, such as a wake word. In certain examples providing voice authentication, the care device 10a-10c verifies the voice against a stored voice signature for each clinician on the list of authorized clinicians. This can be used as a second authentication layer in addition to the location tracking layer.

The list of authorized clinicians is a list of authorized tags, or clinician tag IDs, associated with the clinicians permitted and/or likely to provide care to the infant 22. For example, the list of authorized clinicians may comprise all clinician tags for all clinicians with permission to provide care at a medical facility where the care device 10a-10c is located. In other embodiments, the list of authorized clinicians may be more targeted, such as the list of clinician tags associated with clinicians working in a particular ward or department of the care facility. In still other embodiments, the list of authorized clinicians may be synchronized with a shift schedule such that only those clinicians currently working or on call may be on the list.

In one example, the list of authorized clinicians may be provided and defined by an authorized clinician schedule database 56. The authorized clinician schedule database may store lists of authorized clinician tags, for example, which may be indexed or associatable based on the device location tag 14a-14c and/or the device location. The authorized clinician schedule database 56 may further index the authorized clinician tags based on time-of-day and/or shift schedule, as described above. The authorized clinician schedule database 56 may be stored along with the location authorization module 34 such that it is accessible by the processor executing the location authorization instructions. Thus, the authorized clinician schedule database 56 may be stored locally with the location authorization module 34a-34d. In other embodiments, the authorized clinician schedule database 56 may be stored in the computing system 52 comprising the host network 50, and may be accessible via wireless network connection by the controllers 12a-12c in the respective care devices 10a-10c.

The location authorization module 34 performing the authorization steps may be stored and executed at various computing systems within the infant care system 60. In the depicted example at FIG. 2, each care device 10a-10c comprises a controller 12a-12c, which are each computing systems that store and execute software, including an instance of a location authorization module 34a-34c. In certain embodiments, the location tracking system 40 may communicate a list of one or more local clinician tags to the care device 10a-10c such as via a receiver transmitter 33a-33c in communication with the controller 12a-12c. In such an example, the controller 12a-12c of the respective care device 10a-10c determines whether the local clinician tags identified by the location tracking system 40 are on the list of authorized clinician tags prior to permitted or acting on any user inputs to control or modify the operation of the infant care device. Additional authentication steps or methods may also be executed by the controller 12a-12c, which are variously described herein.

In another embodiment, the location tracking system 40 may provide various clinician locations of clinician tags 17a-17d that are within a larger area around the care device, and the controller 12a-12c of the care device 10a-10c may be configured to determine which clinician tags 17a-17d are within the predefined area 37a-37c around the care device 10a-10c. Thereby, each care device 10a-10c can store and define its own predetermined area 37a-37c and such areas may be adjusted as part of the system configuration, for example.

Alternatively or additionally, the location tracking system 40 may be configured to execute the location authorization module 34d. Thus, in one embodiment, the identification of the local authorized clinician tags may be performed within the location tracking system 40, and such information may be provided to the care devices 10a-10c. In other examples, portion of the location authorization method may be executed within the location tracking system 40, and other portions may be executed locally at the respective care device 10a-10c.

Referring to the example at FIG. 2, multiple clinicians may be moving around in the care environment where the care devices 10a-10c are positioned. For example, the care environment may be a neonatal care environment, such as a neonatal intensive care unit (NICU), where multiple care devices 10a-10c are positioned and are each housing a different infant 22. Accordingly, an authentication method is needed that provides targeted authorization for a specific care device 10-10c intended by a clinician, such as the care device 10a-10c housing the infant 22 for which the clinician is engaging in providing care. The location-based authentication method described herein provides such a targeted authentication solution while also requiring little attention or effort on the part of the clinician and providing immediate, hands-free authentication to an authorized clinician that approaches the care device 10a-10c.

With reference to the scenario depicted in FIG. 2, multiple clinicians wearing clinician location tags 17a-17d are in the care environment, or room, where the care devices 10a-10c are housed. Each care device 10a-10c has an associated predetermined area near the device location that defines the area where the clinician location tags 17a-17d are determined to be local, and thus possibly intending to provide care to the infant 22 and to modify operation of the infant care device 10a-10c. In the example, clinician location tags 17a, 17c, and 17d are within the predetermined area 37a-37c of at least one of the care devices 10a-10c. Clinician location tag 17b is outside of any predefined area, and thus is not determined to be "local" for purposes of authentication. For those local clinician tags 17a, 17c, 17d, steps are executed to determine whether the tags are authorized by comparing the transmitted identifications to the list of authorized clinician tag for the specific care device 10a-10c to which they are local. In the example, clinician location tags 17c and 17d are within the predetermined area 37c around the care device 10c. Thus, clinician location tags 17c and 17d are local clinician tags for the care device 10c and will be compared to the list of authorized clinician tags for that care device 10c to determine whether at least one of the local clinician tags is an authorized clinician tag. If so, then authorization will be provided to modify operation of the infant care device 10c.

In certain crowded care environments, multiple care devices 10a-10c may have overlapping localization areas. In the example, care devices 10a and 10b have predetermined areas 37a and 37b that overlap. Thus, in certain examples, a clinician location tag 17a may be identified as "local" for more than one care device 10a and 10b. In certain embodiments, authentication may be performed and permitted for a single clinician on two care devices 10a and 10b and thus the clinician associated with clinician location tag 17a may be authorized on both care devices at once. In other embodiments, the system 60 may be configured to only permit authorization of a clinician on one care device 10a-10c at a given time. For example, the location authorization module 34 may be configured to first determine with the local clinician tag 17a is currently authorized on any other care device 10a-10c prior to permitting authorization. In other examples, the location authorization module 34 may determine that the local clinician tag 19a is closer to the device location of the care device 10a than to any other device location of any nearby care device 10b, 10c prior to authorization. Thereby, the clinician will only be authorized at the care device 10a-10c to which they are closest.

Alternatively or additionally, the location authorization module 34 may be configured to identify and authorize only a closest local authorized clinician tag within the predetermined area 37a-37c. Thereby, if multiple clinicians are working in an area of the infant 22, only the closest clinician will be authenticated. In still other embodiments, a single local authorized clinician may be identified based on other parameters, such as based on that clinician's role in the care team for the infant 22—e.g., authenticating the tag for a physician when a physician and a nurse are present, or authenticating the clinician tag for a nurse assigned to that patient 22 when multiple nurses are present or when a nurse and a technician are present. In still other embodiments, other parameters may be used to identify a single local authorized clinician, such as the first clinician to arrive within the predefined area 37, seniority, etc.

Figure 3:
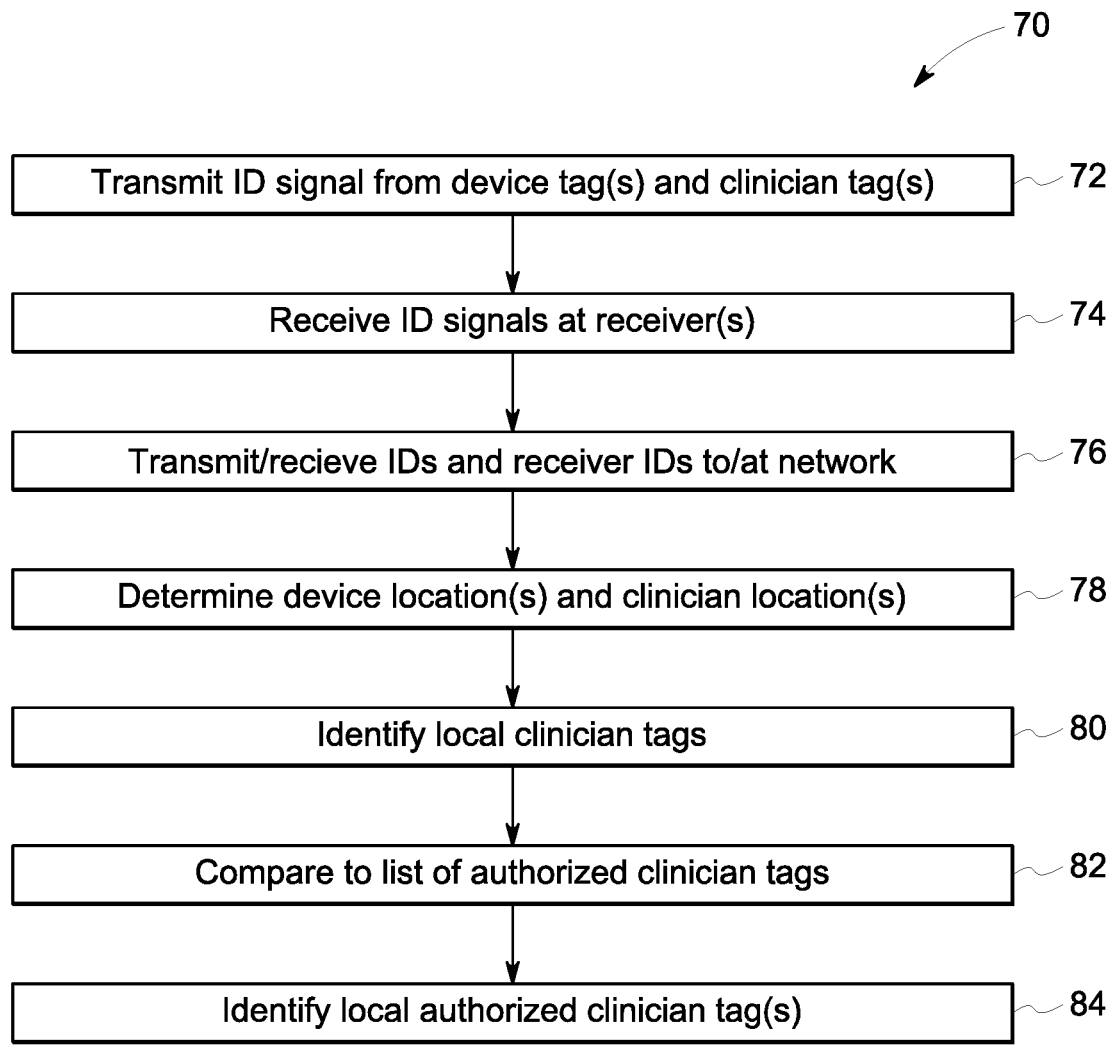
FIGS. 3-6 depict methods, or portions thereof, of controlling an infant care device according to embodiments of the present disclosure.

FIGS. 3-6 depict various embodiments of methods 70, or portions thereof, of controlling an infant care device 10 for location-based authentication. Referring to FIG. 3, steps are executed by the location tracking system 40 in conjunction with the location authorization module 34 to identify local authorized clinicians. An identification signal is transmitted at step 72 from each device tag 14 and clinician tag 17. The identification signals are received at receivers 46 of the location tracking system 40, represented as step 74. The identification signals are then transmitted along with the receiver identifications to the host network 50 or other computing system 52 executing the location tracking software. Represented at step 76, the device and clinician IDs, along with the receiver IDs of one or more relevant receivers 46, are received at the network. The device locations and clinician locations are then determined at step 78 based on the receiver IDs. The time of receipt at each receiver may also be included and triangulation calculations may be performed to determine a precise location of the device tags 14 and clinician tags 17, and their relative locations to one another. Such methods are well known with respect to location tracking systems, such as RTLS systems.

At least one local clinician tag is then determined at step 80 by identifying the one or more clinician location tags 17 that are within the predetermined area 37 with respect to the device location defined by the detected device location tag 14. The local clinician tags are then compared to a list of authorized clinician tags at step 82. Based on the comparison, local authorized clinician tags are identified at step 84. In certain embodiments, authorization and permission to modify operation of the infant care device may be granted upon detection of at least one local authorized clinician tag. In other embodiments, additional logic may be applied prior to providing authorization and/or allowing modification to the operation of the infant care device or other interactions with the user interface 29 of the infant care device, such as requiring a wake word or further verifying that the authorized clinician is not currently authorized for any nearby care device 10.

Figure 4:
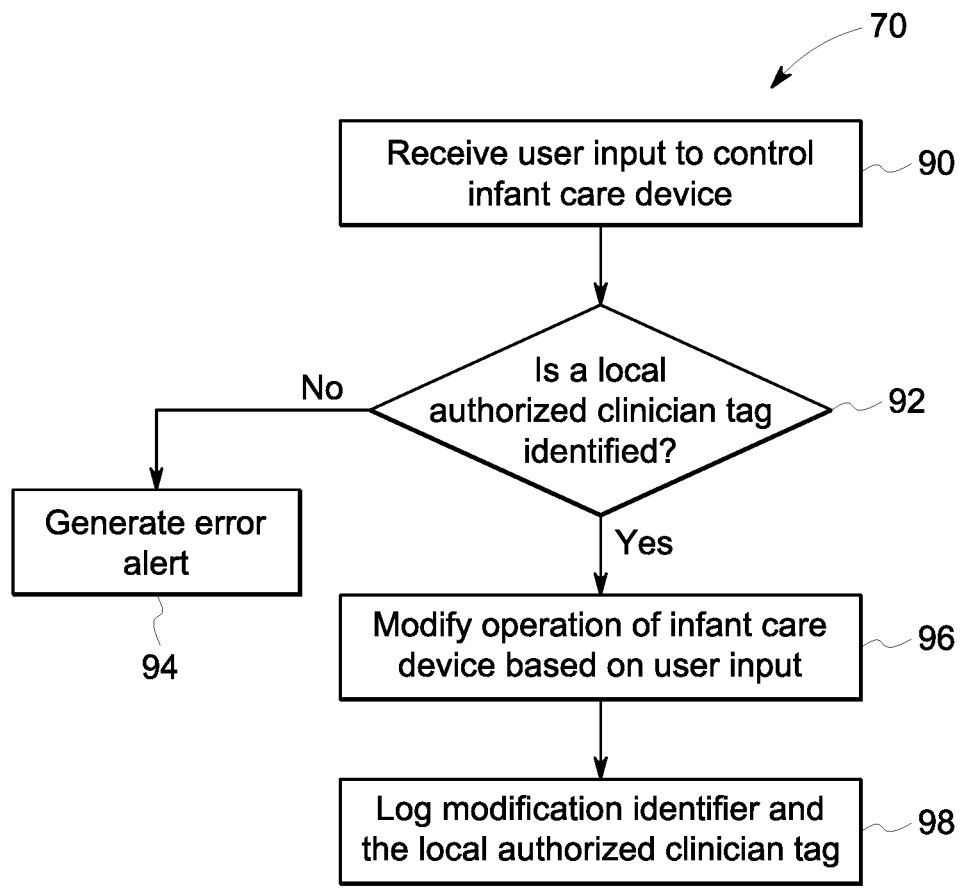
Figure 5:
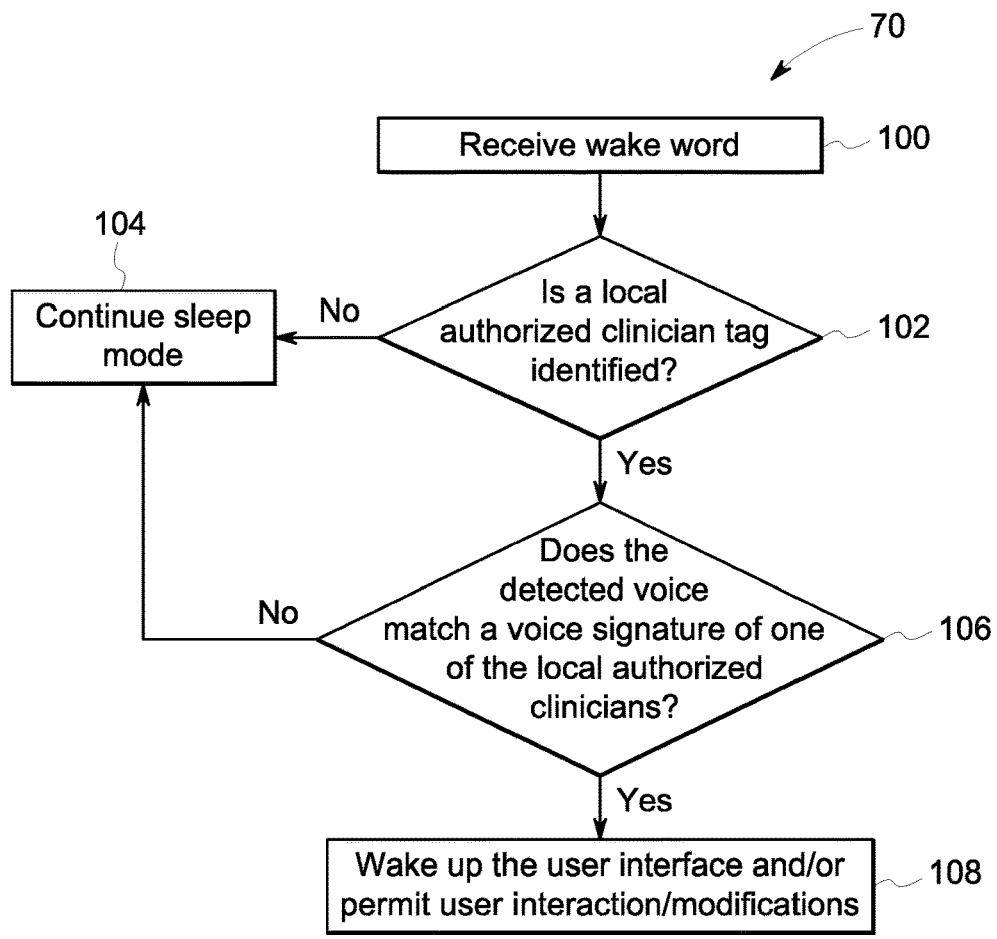

FIG. 4 depicts exemplary authorization steps that may be performed by the location authorization module 34, such as the location authorization module 34a-34c executed on a respective care device 10a-10c. User input is received at step 90 to control the infant care device. For example, user input may be received via the user interface 29 on a respective care device 10, such as to control an environmental parameter where the micro environment 16, to request display of identification or health information of the infant 22, or to modify the infant's medical record. An inquiry is conducted at step 92 to determine whether a local authorized clinician tag is identified, such as utilizing the results of the steps represented at FIGS. 3, 5, and/or 6. If no local authorized clinician tag is identified, then an error alert may be generated at step 94. For example, the display 28 may display a visual error alert to alert the user providing input that no authorization is granted. Alternatively or additionally, the error alert may be auditory alert provided via one or more user interface devices associated with the care device 10.

If a local authorized clinician tag at step 92, then action is taken based on the user input to modify operation of the infant care device at step 96. A corresponding modification identifier is logged at step 98 along with the local authorized clinician tag, such as the clinician ID of each of the one or more authorized clinicians identified at the time of receiving the user input. The modification identifier is, for example, a description of the modification or an identification code that is associated with a particular modification.

Figure 6:
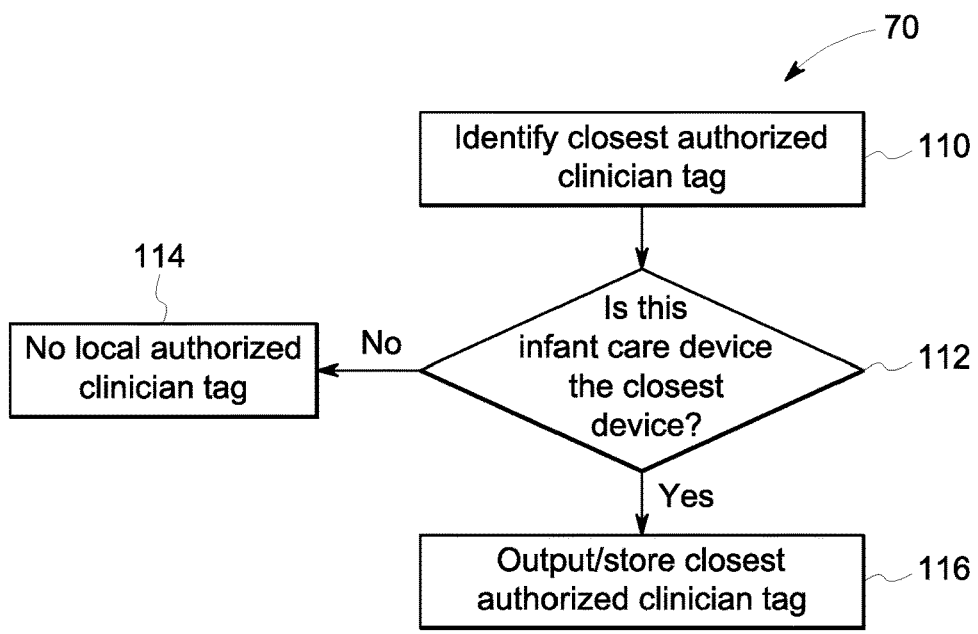

In certain embodiments, voice recognition and/or voice command functionality may be utilized in conjunction with the location authentication methods, such as those steps represented at FIG. 3 and/or FIG. 6. A wake word is received at step 100, such as by a voice recognition system 32 on the care device 10 at step 100. An inquiry is performed at step 102 to determine whether a local authorized clinician is identified, according to various embodiments described herein. If no local authorized clinician is identified, then the device 10 is maintained in sleep mode at step 104. For example, the user interface 29 of the care device 10 may remain unresponsive to inputs from the user, and no modification of the operation of the care device 10 will be performed in response to the user input. In certain embodiments, the system may be "woken up" upon receipt of the wake word and identification of at least one authorized clinician. In other embodiments, if a local authorized clinician tag is identified, then instructions are performed at step 106, such by the voice recognition system 32, voice authentication may also be performed to determine whether the detected voice matches a voice signature of one of the local authorized clinicians. If the detected voice does not match the relevant voice signature(s), then the sleep mode is continued at step 104. If the wake word is received and the voice does match, then the user interface 29 may be activated, or "woken up," at step 108 to permit user control of the care device 10. In other embodiments, the voice detection and/or voice authentication step(s) may occur prior to the steps of identifying the local authorized clinician tag, and the identified clinician based on the voice signature may be matched to the local clinician tags in order to permit authorization.

FIG. 6 represents steps that may be performed as part of the authorization for a local clinician. In the depicted example, a closest authorized clinician tag is identified at step 110, which may be the clinician location tag 17 closest to the device location tag 14, for example. In other embodiments, the method may account for the area occupied by the care device 10 and the location of the device tag 14 on the care device 10, and may determine a closest clinician tag 17 to the care device 10, itself. Once the closest authorized clinician tag is identified, instructions may be executed to determine whether the infant care device performing the authorization is the closest device to that clinician location tag 17. Thereby, a clinician will only be authenticated at the care device 10 to which that clinician is closest. Referring to the example of FIG. 2, for instance, the clinician wearing clinician location tag 17a would only be authenticated at care device 10a, which is the closest care device for that clinician. Thus, even though the clinician location tag 17a is within the predetermined areas 37a and 37b, utilizing this method of FIG. 6, the clinician 17a would not be authenticated on the care device 10b because that clinician location tag 17a is closer to care device 10a.

Referring again to FIG. 6, if the closest authorized clinician tag (e.g. 17a) is not closest to the device seeking authorization, then the authorization will not be granted and no local authorized clinician tag will be detected, as represented at step 114. Accordingly, authorization may be denied and, in certain embodiments, an error alert may be generated. If the closest authorized clinician tag is indeed closer to the care device 10 performing the authorization, then such authorization is granted at step 116 and the closest authorized clinician tag will be outputted and/or stored. In other embodiments, the instructions represented at step 112 may be performed independently of the determination of the closest authorized clinician tag so as to verify that each clinician tag 17a-17d is only authorized at one care device 10a-10c at any given time.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An infant incubator or warmer comprising:
   a platform configured to support an infant;
   an environmental control system configured to control a temperature and/or humidity of an environment around the infant;
   a user interface configured to receive a user input to control operation of the infant incubator or warmer;
   a controller configured to receive the user input from the user interface and to control operation of the infant incubator or warmer, wherein the controller is configured to:
   receive the user input from the user interface to control operation of the infant incubator or warmer;
   determine that the user input is a request to modify operation of the infant incubator or warmer that includes adjusting operation of the environmental control system and, in response thereto, determine whether at least one authorized clinician is within a predetermined area around the infant incubator or warmer based on clinician information from a real time location tracking system;
   wherein the clinician location information from the location tracking system includes a list of one or more local clinician tags that are within the predetermined area around the infant incubator or warmer with each clinician location tag configured to be on a respective clinician, and wherein the controller is further configured to compare the list of one or more local clinician tags, including a closest local authorized clinician tag, to a list of authorized clinician tags to determine whether the at least one authorized clinician is within the predetermined area around the infant incubator or warmer;
   if at least one authorized clinician is within the predetermined area around the infant incubator or warmer, modify the operation of the infant incubator or warmer based on the user input; and
   if no authorized clinician is within the predetermined area around the infant incubator or warmer, do not modify the operation of the infant incubator or warmer based on the user input.

2. The infant incubator or warmer of claim 1, wherein the controller of the infant incubator or warmer is further configured to generate an error alert upon receipt of the user input to control operation of the infant incubator or warmer when no authorized clinician is within the predetermined area.

3. The infant incubator or warmer of claim 1, wherein the controller is further configured to log a modification identifier and the at least one authorized clinician, wherein the modification identifier identifies the modification of the infant incubator or warmer based on the user input.

4. The infant incubator or warmer of claim 1, wherein the clinician location information from the location tracking system includes the closest local authorized clinician tag within the predetermined area of the infant incubator or warmer.

5. The infant incubator or warmer of claim 1, wherein the user interface includes a voice recognition system configured to detect a wake word from a clinician associated with the at least one authorized clinician, wherein the controller is further configured to determine whether the at least one authorized clinician is within the predetermined area around the infant incubator or warmer upon receipt of the wake word.

6. The infant incubator or warmer of claim 5, wherein the controller is further configured to require receipt of the wake word prior to modifying operation of the infant incubator or warmer.

7. The infant incubator or warmer of claim 1, wherein the user interface is further configured to display patient identification information and medical record information for the infant on a display;
   wherein the controller is configured to prevent display and/or modification of the patient identification information and/or the medical record information via the user interface when no authorized clinician is within the predetermined area.

8. An infant care system comprising:
   an infant care device including:
   a controller that controls operation of the infant care device;
   a user interface configured to receive user input to control operation of the infant care device;
   a device location tag on the infant care device;
   multiple clinician location tags, each clinician location tag configured to be worn on a respective clinician;
   a real time location tracking system configured to:
   identify a device location of the infant care device within a care facility by locating the device location tag;
   identify any local clinician tags, wherein a local clinician tag is one of the multiple clinician location tags that is within a predetermined area around the device location;
   a location authorization module executable by the controller to compare the local clinician tags to a list of authorized clinicians to identify at least one local authorized clinician tag, including a closest local authorized clinician tag;

wherein the controller of the infant care device is configured to determine whether the user input is a request to modify operation of the infant care device that includes adjusting operation of an environmental control system of the infant care device and, in response thereto, determine whether the at least one local authorized clinician tag is within the predetermined area around the infant incubator or warmer based on clinician location information from the real time location tracking system, and modify operation of the infant care device based on the user input to control operation of the infant care device only when the at least one local authorized clinician tag is identified within the predetermined area around the infant care device and to not modify operation of the infant care device based on the user input when no local authorized clinician tag is identified within the predetermined area around the infant care device.

9. The system of claim 8, wherein the controller of the infant care device is further configured to generate an error upon receipt of the user input to control operation of the infant care device when no local authorized clinician tag is within the predetermined area.

* * * * *